(12) United States Patent
Fields et al.

(10) Patent No.: US 7,311,677 B1
(45) Date of Patent: Dec. 25, 2007

(54) ENERGY CONCENTRATOR SYSTEM AND METHOD

(76) Inventors: John G. Fields, 383 Corral De Tierra, Salinas, CA (US) 93908; Philip A. Dalton, 115 San Rafael Way, San Francisco, CA (US) 94127

( * ) Notice: Subject to any disclaimer, the term of this patent is extended or adjusted under 35 U.S.C. 154(b) by 228 days.

(21) Appl. No.: 10/186,182

(22) Filed: Jun. 26, 2002

(51) Int. Cl.
*A61N 7/00* (2006.01)
(52) U.S. Cl. .............................. 601/2; 601/4; 367/142; 367/151; 367/171
(58) Field of Classification Search ................ 600/407, 600/437, 439, 473–478; 601/2, 3, 4; 367/142, 367/147, 171, 174, 150, 151
See application file for complete search history.

(56) References Cited

U.S. PATENT DOCUMENTS

| | | | | |
|---|---|---|---|---|
| 4,697,588 A | * | 10/1987 | Reichenberger | 601/4 |
| 4,721,108 A | * | 1/1988 | Heine et al. | 601/4 |
| 5,156,144 A | * | 10/1992 | Iwasaki et al. | 601/4 |
| 5,174,280 A | * | 12/1992 | Gruenwald et al. | 601/4 |
| 6,755,796 B2 | * | 6/2004 | Spector | 601/2 |

* cited by examiner

*Primary Examiner*—Ruth S. Smith

(57) ABSTRACT

Reflective apparatus and method by which energy is radiated in divergent fashion from an elongated source and is reflected by a first parabolic reflector as a paraxial beam, focused by a second parabolic reflector onto a hyperbolic reflector and reflectively concentrated by the hyperbolic reflector at a focus at a distance from the source. The system also shields the point from extraneous radiation that would not be concentrated at the point. In one exemplary application, electromagnetic energy radiated from a point or linear source is focused by the multiple reflector system to a very high concentration at a point, for example, within an organism such as a human or animal body.

13 Claims, 3 Drawing Sheets

ENERGY CONCENTRATOR SYSTEM AND METHOD

BACKGROUND OF THE INVENTION

1. Field of the Invention

The present invention relates in general to systems for concentrating energy and, more particularly, to systems for concentrating electromagnetic energy.

The present invention also relates to systems and methods for concentrating energy for the purpose of destroying tumors and other undesirable growths.

2. Description of the Related Art

Prior art systems which project energy into the body to destroy tumors, etc. typically suffer from the inability to precisely focus the energy at high concentrations inside the body and to destroy the target without injury to the surrounding tissue and skin.

RF energy offers the potential advantage of high power, but it is difficult to focus RF energy, and especially difficult to focus such energy without absorption in surrounding media. More specifically, the prior art of focusing RF energy to a point/point volume from a source has been a challenge because of the divergent nature of the radiation pattern and frequency wavelength. In so-called non-invasive surgery applications, RF radiation may be directed by induction into a human body and allowed to cover a larger volume than the tumor or other target, thus affecting healthy tissue and organs. In some cases the healthy tissue is heated severely and/or experiences severe side effects. It is thought to be as the result of these difficulties that RF systems have not been used successfully for applications such as non-invasive surgery.

SUMMARY OF THE INVENTION

In one aspect, the present invention is embodied in apparatus and methods for reflectively concentrating a large amount of energy emanating from an elongated source to a very small focus. Preferably the focus is or approximates a point.

In another aspect, the present invention is embodied in reflector apparatus and methods for broadcasting or emitting energy from a source, reflecting that energy as a near-paraxial beam, then concentrating that beam to a focus, which, in a preferred embodiment, is a point focus. The energy can be from sources of electromagnetic energy over a wide range of frequencies including but not limited to RF frequencies and to radiant heat frequencies; acoustic sources; and radioactive sources.

In another apparatus or system aspect, the present invention is embodied in an optical reflector system for concentrating energy at a point, comprising: {a} source generating a point of energy radiated divergent from the source; {b} a first parabolic reflector having a concave reflector surface and a focal point, the concave reflector being positioned with the focal point thereof coincident with the source and oriented to intercept energy from the source such that the intercepted energy is reflected in a paraxial beam; {c} second parabolic reflector having a concave reflector surface and a focal point, the concave surface of the second parabolic being positioned and oriented to intercept the path of the paraxial beam, such that energy comprising the beam is reflected toward the focal point of the second parabolic reflector; and {d} a hyperbolic reflector having a convex reflector surface and having first and second focal points. The hyperbolic reflector is positioned and oriented with the convex reflector surface thereof intercepting the path of energy reflected from the second parabolic reflector and is positioned with the first focal point thereof coinciding with the focal point of the second parabolic reflector, for reflecting energy from the second parabolic reflector and concentrating said energy at the second focal point of the hyperbolic reflector.

In other, apparatus or system aspects, the invention is embodied in dish or toroidal configurations, or in linear, trough-like configurations, either straight or curved.

In a method aspect, the present invention is embodied in a method for reflecting energy from a source to first and second parabolic reflectors and a hyperbolic reflector and focusing the energy to a point focus a distance removed from the source. The method comprises: providing a source of spatially divergent radiated energy; at a first parabolic reflector, which is oriented concavely with respect to the source, intercepting energy from the source and reflectively forming the energy into a paraxial beam; at a second parabolic reflector, which is oriented concavely relative to the paraxial beam, intercepting the parabolic beam and reflectively focusing the energy comprising the paraxial beam toward a first focal point of a hyperbolic reflector, which is oriented convexly relative to the beam reflected from the second parabolic reflector. At the hyperbolic reflector, energy reflected from the second parabolic reflector is intercepted and reflectively focused at a second focal point of the hyperbolic reflector.

In yet another aspect, the present invention is embodied in apparatus and methods which utilize RF frequencies of varying wavelengths and focuses the energy to a point volume with little focus of energy on adjacent areas and volumes, such as adjacent healthy tissue. This is accomplished by capturing the divergent energy inside a housing, by intercepting divergent RF energy radiated from a focal line/source at one parabolic curve and reflecting a portion of the energy into paraxial radiation directed toward a second parabolic curve. Upon reflection at the second parabolic curve, the energy is directed towards one focal point of a hyperbolic curve which focal point coincides with the focal point of the second parabolic curve. The energy is thus directed to the second focal point of the hyperbolic curve and to a point volume or point.

The use of a source in the shape of a circle and a thin line source allows the use of many different frequencies and wavelengths, both RF and others. Other phenomenologies, such as acoustics/sound, electromagnetic radiation at light frequencies and nuclear particles can be focused using this approach. In short, the reflective housing focuses divergent energy from elongated sources to a point and the elongated source configuration permits the use of a wide assortment of energy sources and high energy input for the point focus output.

The apparatus and methods of the present invention allow the use of antenna design to increase efficiency by increasing the capture within the system of divergent energy from the input or source and by focusing the energy to a point or point volume output and attenuating the energy loss to surrounding regions or volumes.

BRIEF DESCRIPTION OF THE DRAWING

The present invention is described with respect to the drawings, in which.

DETAILED DESCRIPTION OF THE PREFERRED EMBODIMENT(s)

In one aspect the present invention relates to the combination of (1) a particular energy source, preferably an elongated source, which permits the input of large amounts of energy to the system and (2) a point focus of the energy, specifically concentrating the energy to a point focus and thus to a very high concentration at a precisely defined location. It is critical to keep in mind the difference between the energy source (the input) on the one hand, and the energy focus (the output) on the other hand.

In reference to the present invention and with specific regard to the output or focus, the phrase "point focus" includes a focus of small cross-section which approximates a point focus.

With specific regard to the input or source, the phrase "elongated source" refers to both linear and arcuate sources of small transverse cross-section, that is, to elongated sources which are or approximate a point source in the transverse dimension. It is understood that such a source functions as a point source in the transverse dimension. For convenience, "linear source" may be used in the generic sense to encompass both arcuate and straight sources.

Figure 1:
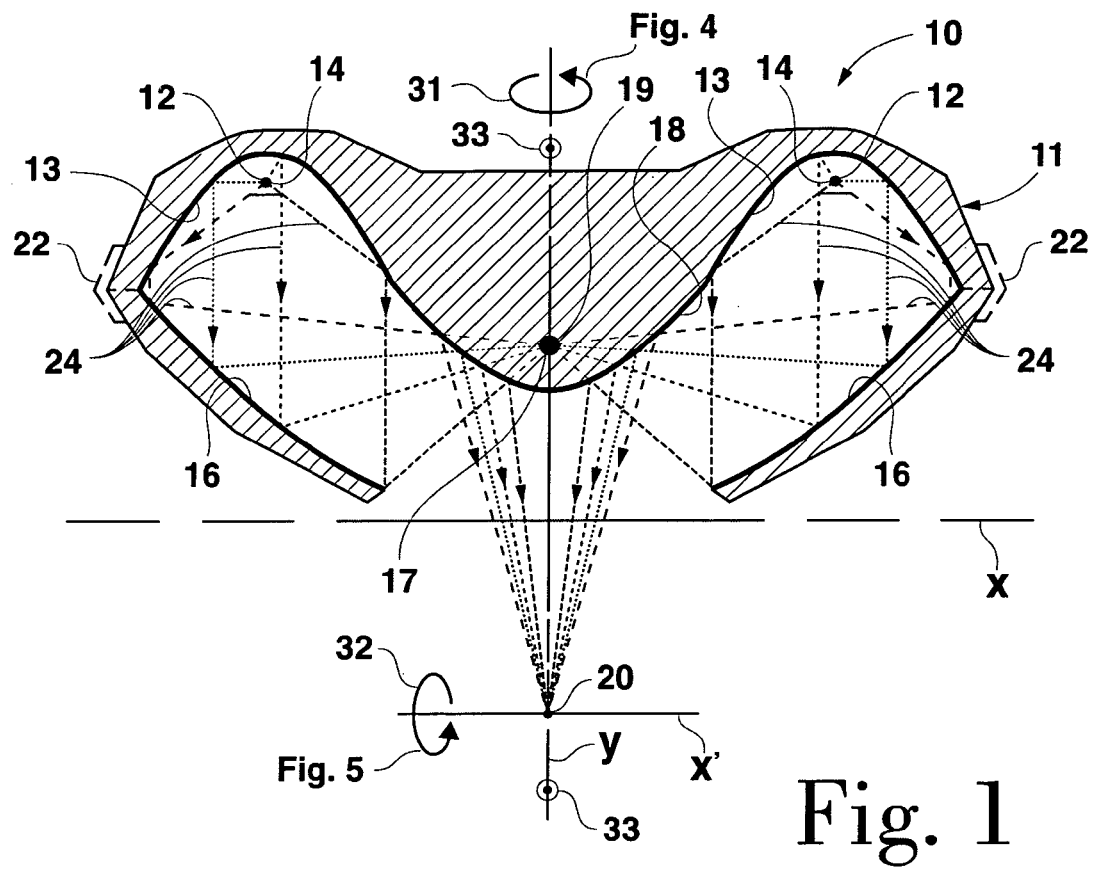
FIG. 1 is a cross-section view of an energy concentrator unit embodying the present invention, taken in the direction of the arrows 1—1 in FIGS. 4, 5, 7 and 8.

Referring to FIG. 1, there is shown a cross-section of a reflector energy concentrator unit and system (ecu) 10 which embodies the present invention. The ecu 10 comprises a housing 11, a point source 12 (here a linear source which in section is a point source) that provides a near point source of divergent radiating energy; a primary parabolic reflector/mirror 13 having a focal point 14 and a concave parabolic reflecting surface (concave to incident energy or radiation) formed to the general parabolic equation $y=nx^2$; a secondary parabolic reflector/mirror 16 also having a focal point 17 and a concave reflecting surface (concave to incident energy or radiation) formed to the general parabolic equation $y=nx^2$; and a hyperbolic reflector/mirror 18 having first and second focal points 19 and 20 and having a convex hyperbolic reflecting surface (convex to incident energy or radiation) formed to the general hyperbolic equation $y^2/a^2-x^2/b^2=1$. Energy of whatever type that is input at source(s) 12 and is focused by the energy concentrator unit at 20.

The point source 12 may be a source of electromagnetic, acoustic or other energy. The parabolic and hyperbolic reflectors may comprise a concave surface (concave to incident energy radiation) or convex surface (convex to incident energy or radiation) which is highly reflective. For example, the reflectors may comprise material such as aluminum having a surface which is polished or otherwise made highly reflective. Alternatively, the reflectors may comprise a base or support on which is formed or deposited a highly reflective coating (not shown) of material such as aluminum or gold or other suitable reflective material.

Figure 2:
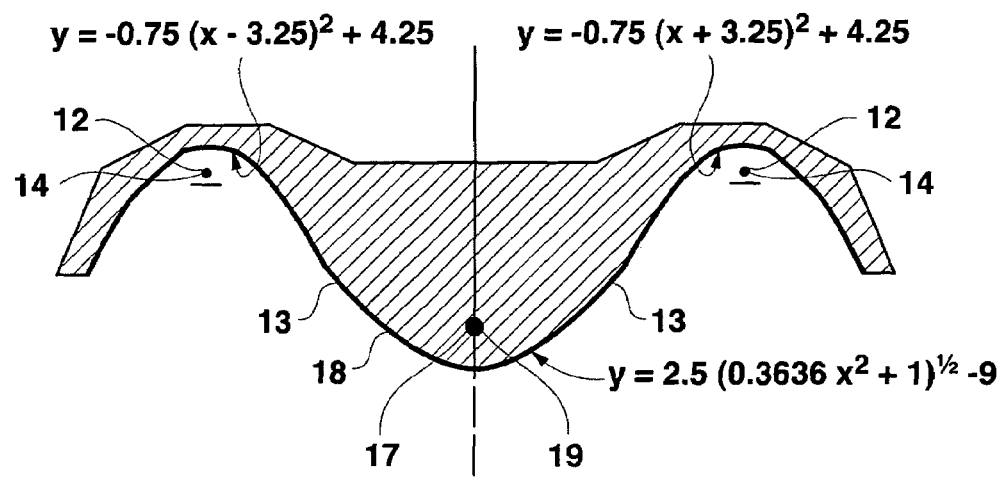
FIGS. 2 and 3 are enlarged depictions of two mating (top and bottom) sections that together form an energy concentrator unit of the type depicted in FIG. 1.
Figure 3:
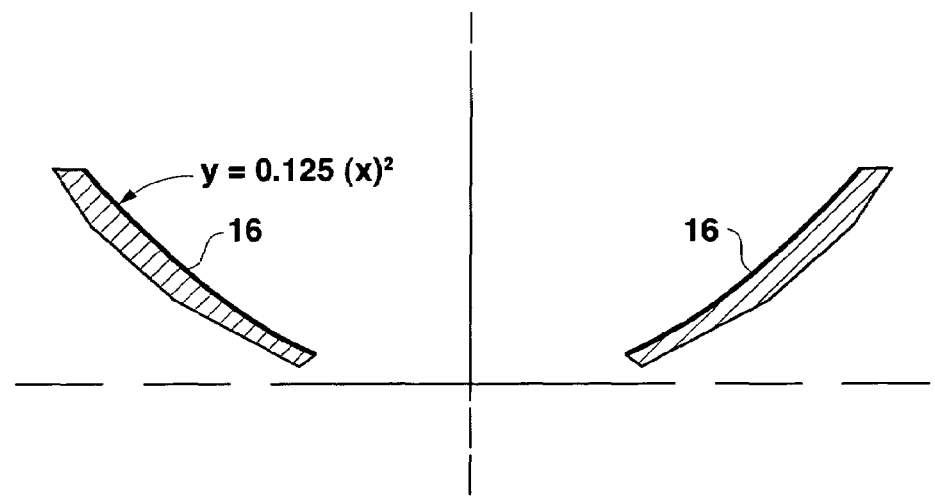

Referring also to FIGS. 2 and 3, the reflectors may be an integral unit (FIG. 1) or may be part of a housing which is assembled from sections (FIGS. 2 and 3). This latter approach facilitates manufacture, especially formation of the reflectors, but requires precise assembly and mounting of the sections in the proper orientation and position. Alternatively, the housing can be formed by casting or molding using metal or plastic. The integral reflector surfaces can be formed by polishing or by application of a high-reflectivity layer.

In one embodiment, brackets having arms oriented at the appropriate orientation of the two sections may be used to mount the sections. Although FIG. 1 depicts an integral unit, an exemplary hinge 22 is shown there in phantom to illustrate the manner in which the sections of FIGS. 2 and 3 would be assembled to provide the positioning and the angular relationships of FIG. 1.

System Operation (Ray Trace)

Referring in particular to FIG. 1, the equations of the reflectors are determined such that, with the source 12 positioned proximate the primary parabolic reflector 13, specifically, with the source at the focal point 14 of the primary parabolic reflector, energy radiating from the source is reflected from the primary parabolic reflector as a paraxial beam 24. The beam 24 is illustrated by parallel ray traces 24—24 in FIG. 1.

The concave secondary parabolic reflector 16 and the convex hyperbolic reflector 18 are positioned with their focal points 17 and 19 coincident, that is the focal point 17 of the secondary parabolic reflector 16 coincides with a first 19 of the two focal points of the convex hyperbolic reflector 18. As a result, the paraxial beam 24 emanating from the primary parabolic reflector 13 is reflected from the secondary parabolic reflector 16, is intercepted by and reflected off the convex hyperbolic reflector 18, and is focused, is concentrated, at the second focal point 20 of the convex hyperbolic reflector.

In summary, as alluded to above, as the result of the use of the above-described multiple reflector concentrator unit, energy emitted from a point source 12 is reflected by the primary parabolic reflector as a paraxial beam, is then reflected and focused by the secondary parabolic reflector toward the first focal point 19 of the hyperbolic reflector, then is reflected and focused by the hyperbolic reflector to the second focus 20 of the hyperbolic reflector.

Summary of Certain Applications of the Energy Concentrator Unit

Different configurations of the energy concentrator unit 10 are depicted in FIG. 4–8.

Figure 4:
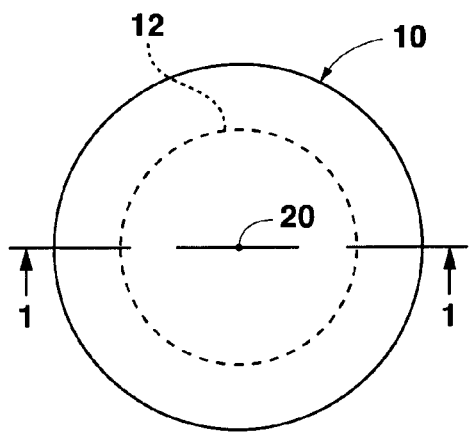
FIG. 4 is a simplified schematic representation of a dish-type reflector energy concentrator unit and system in accordance with the present invention.

The embodiment of FIG. 4 comprises a dish. The cross-section of view of FIG. 1 is taken in the direction of the arrows 1—1, tht is, in the direction of the lines 1—1 in FIG. 4. The FIG. 4 dish configuration conceptually is the result of rotating the FIG. 1 x'y cross-section about the y-axis, FIG. 1, as shown by rotational arrow 31. The dish can be a full circle configuration (360°) or a segment of a circle (<360°).

Figure 5:
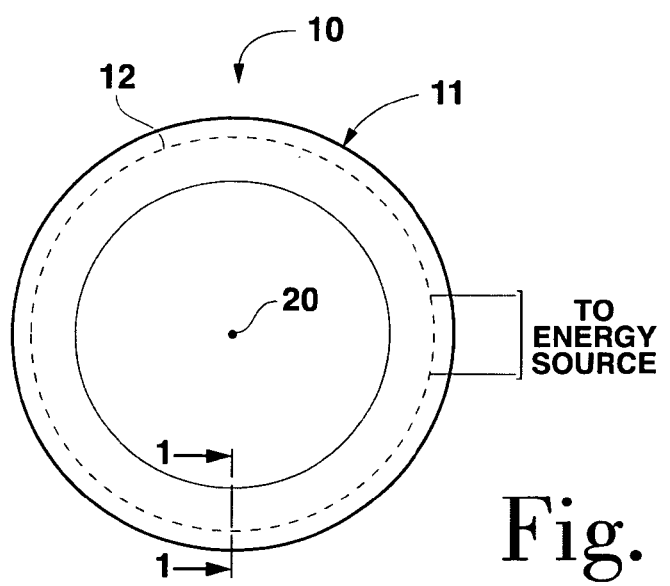
FIG. 5 is a simplified schematic representation of a toroidal-shaped reflector energy concentrator unit and system in accordance with the present invention.
Figure 6:
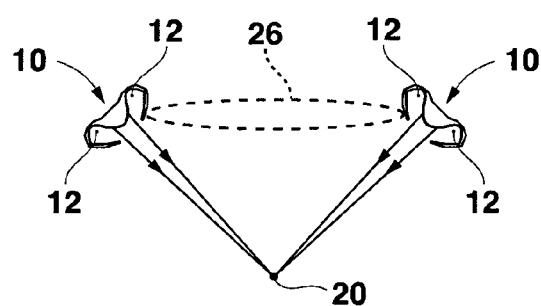
FIG. 6 is a simplified schematic representation of an alternative toroidal-shaped (or dish or trough-shaped) reflector energy concentrator unit and system in accordance with the present invention.

The embodiments of FIGS. 5 and 6 and comprise doughnut or toroid-shaped configurations. The cross-section view of FIG. 1 is taken in the direction of the arrows 1—1, in the direction of lines 1—1, in FIGS. 5 and 6. The FIG. 5 toroidal configuration conceptually is the result of rotating the FIG. 1 x'y cross-section about the x'-axis of FIG. 1, as indicated by arrow 32.

As alluded to above, in FIG. 6, the reflector surfaces are angled to focus the energy from the source(s) to a point or a line outside (here, below) the energy concentrator unit. As shown in phantom, a magnifying lens 26 can be incorporated within the housing of the energy concentrator unit to permit inspection and/or control of the focus 20. This arrangement is useful, e.g., for monitoring and/or controlling the positioning of the energy concentrator unit during manual or automatic welding or other joining operations. Please note, the configuration of FIG. 6 is also applicable to linear systems of the type shown in FIGS. 7 and 8, and to dish systems of the type shown in FIG. 4.

Figure 7:
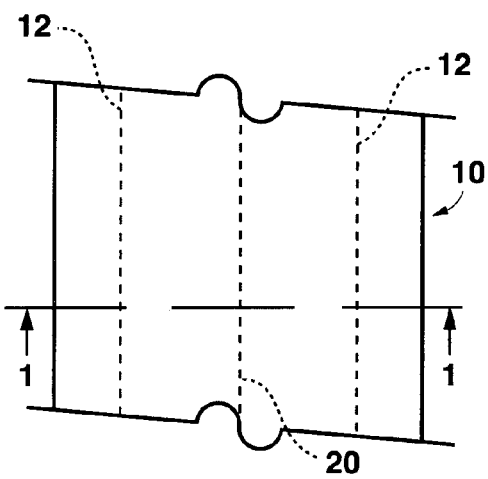
FIG. 7 is a simplified schematic representation of a straight linear, trough-like reflector energy concentrator unit and system in accordance with the present invention.
Figure 8:
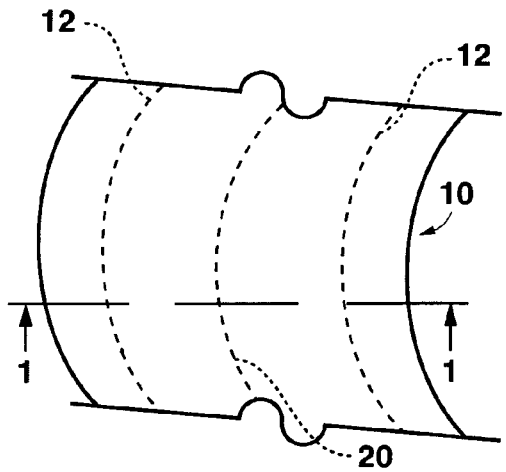
FIG. 8 is a simplified schematic representation of an arcuate linear, trough-like reflector energy concentrator unit and system in accordance with the present invention.

FIGS. 7 and 8 depict, respectively, straight and arcuate trough-type energy concentrator units. Again, The cross-section view of FIG. 1 is taken in the direction of the arrows 1—1, in the direction of lines 1—1, in the associated figures, here FIGS. 7 and 8. Please note, multiple adjacent longitudinal or transversely oriented straight or curved energy concentrator units can be incorporated in the configurations of FIGS. 7 and 8. The reflectors can be angled as shown in FIG. 6, to provide single or plural linear foci of energy. The straight and arcuate troughs conceptually are the result of translating the x'y cross-section of FIG. 1 along straight or curved axes 33—33 transverse to the plane of FIG. 1.

The above dish and toroid configurations are illustrated in FIGS. 4–6 as closed circles, that is, as 360° embodiments. These configurations can effect a very high concentration of energy at the point focus. Alternatively, one or more sections, each spanning less than 360°, can be used, for providing a lesser concentration of energy and/or for applying different types of energy or energy of different frequencies to the various sources simultaneously or at selected times. This permits very precise control of the energy at the focus. The same approach can be applied to the straight and arcuate trough-type sources of FIGS. 7 and 8.

The above embodiments are representative of the various embodiments that are possible for the energy concentrator unit of the present invention. These embodiments are especially useful for selectively destroying or partially destroying growths on or inside a body such as the human body or animal bodies in general, and for applying energy to achieve precision automatic or manual joining or welding.

EXAMPLE

An exemplary circular reflector unit 10 of the type depicted in FIG. 4 and which effects the above described energy concentration, expressed mathematically, comprises two primary (or first) parabolic reflectors 13—13 of equation $y=-0.75(x-3.25)^2+4.25$ (left side parabolic, FIGS. 1 and 2) and $y=-0.75(x+3.25)^2+4.25$ (right side parabolic, FIGS. 1 and 2); two secondary (or second) parabolic reflectors 16—16, both of the equation $y=0.125x^2$ (FIGS. 1 and 3); and a hyperbolic reflector 18 of equation $y=2.5(0.3636x^2+1)^{1/2}-1$ (FIGS. 1 and 2).

SUMMARY

The energy concentrator unit can be dish shaped, as shown in FIG. 4), in which case the focus 20 is preferably a point. Alternatively, the energy concentrator unit can be doughnut or toiroidal-shaped body, FIGS. 5 and 6, with the focus 20 preferably being a point within the torus (FIG. 5) or a point outside the torus (FIG. 6). The energy concentrator unit can be configured in a straight linear configuration, e.g., the straight trough depicted schematically in FIG. 7 having one or a plurality of generally straight sources 12. This provides a separate linear focus for each linear source 12 or, by angling the reflectors inwardly as depicted in FIG. 6, provides overlapping foci for the individual sources 12 and a single linear focus of energy or plural linear foci of energy. In yet another alternative embodiment, not exhaustive, the energy concentrator unit can be configured in a curved configuration, e.g., the arcuate trough depicted schematically in FIG. 8 having one or a plurality of curved sources 12, to provide a separate arcuate focus for each linear source 12 or, by angling the reflectors inwardly as depicted in FIG. 6, to provide overlapping foci and a single arcuate focus of energy or plural arcuate foci of energy. Thus, depending upon the configuration of the ecu 10, energy of whatever type from the source(s) is concentrated into one or a plurality of points or straight lines or arcuate lines or combinations thereof.

Having thus described a reflective beam propagation system and applications thereof, all in accordance with the present invention, those of usual skill in the art will adapt the invention to and derive other embodiments limited solely by the claims appended hereto.

What is claimed is:

1. An energy concentrator, comprising:
   an elongated source of divergent emitted energy; and a housing surrounding the source and comprising internal reflector surfaces capturing the divergent energy and concentrating the divergent energy from the source to a point focus;
   the housing further comprising an aperture; the point focus being external to the housing; the internal reflector surfaces being adapted for focusing the divergent energy through the aperture to the point focus;
   wherein the internal reflector surfaces include a first parabolic reflector, a second parabolic reflector and a hyperbolic reflector.

2. The energy concentrator of claim 1, wherein the elongated source is linear and the first and second parabolic reflectors and the hyperbolic reflector are arranged in a corresponding linear configuration.

3. The optical reflector system of claim 1, wherein the source is arcuate and the first and second parabolic reflectors and the hyperbolic reflector are arranged in a corresponding arcuate configuration.

4. The optical reflector system of claim 1, wherein the source is circular and the first and second parabolic reflectors and the hyperbolic reflector are arranged in a toroid configuration such that said second focal point of the hyperbolic reflector is located within the plane of the circle for concentrating the energy within the plane of the circle.

5. The optical reflector system of claim 1, wherein the source is circular and the first and second parabolic reflectors and the hyperbolic reflector are arranged in a circular configuration such that said second focal point of the hyperbolic reflector is located external to the plane of the circle for concentrating the energy external to the plane of the circle.

6. An energy concentrator, comprising:
   an elongated source emitting divergent energy; and a housing surrounding the source, the housing comprising first reflector means for converting to a paraxial beam energy broadcast or emitted by the source, and second reflector means for focusing the beam to a point;
   the first reflector means comprising a first parabolic reflector having a concave reflector surface and a focus, the first parabolic reflector being positioned with the focus thereof coincident with the source and with the concave reflector surface thereof oriented to intercept energy from the source such that the intercepted energy is reflected in a paraxial beam; and the second reflector means comprising a second parabolic reflector having a concave reflector surface and a focus, the concave reflector surface of the second parabolic reflector being positioned to intercept the path of the paraxial beam and oriented to reflect the beam toward the focus of the second parabolic reflector; and a hyperbolic reflector having a convex reflector surface and having first and second foci, the hyperbolic reflector positioned with the convex reflector surface thereof intercepting the path of energy reflected from the second parabolic reflector and with the first focus thereof coinciding with the focus of the second parabolic reflector for reflecting energy reflected from the second parabolic reflector and concentrating the energy reflected from the second parabolic reflector at the second focus of the hyperbolic reflector.

7. The energy concentrator of claim 6, the second focus of the hyperbolic reflector being external to the housing.

8. An energy concentrator, comprising: an elongated source of divergent radiated energy; and a housing surrounding the source; the housing comprising internal reflector surfaces; and the internal reflector surfaces including a first parabolic reflector for intercepting the divergent energy from the source and reflectively producing a paraxial beam therefrom; a second parabolic reflector having a focal point, the second parabolic reflector being positioned for reflectively focusing the paraxial beam of energy toward the focal point of the second parabolic reflector; and a hyperbolic surface having first and second focal points, the hyperbolic surface being positioned with the first focal point thereof coincident with the focal point of the second parabolic surface, for intercepting the energy focused by the second parabolic reflector and reflectively concentrating the intercepted energy to the second focal point.

9. A reflector system for concentrating energy, comprising:
    an elongated source generating energy radiated divergent from the source;
    a first elongated parabolic reflector having a reflector surface which is of concave parabolic profile in transverse cross-section and forms an elongated focus, the first parabolic reflector being positioned and oriented with the elongated focus thereof coincident with the elongated source for intercepting energy from the source and reflecting the intercepted energy as a paraxial beam;
    a second elongated parabolic reflector having a reflector surface which is of concave parabolic profile in transverse cross-section and forms a focus, the second parabolic reflector being positioned and oriented for intercepting the path of the paraxial beam and reflecting and focusing the beam toward the focus of the second parabolic reflector; and
    a hyperbolic reflector having a reflector surface which is of convex hyperbolic profile in transverse cross-section and having first and second foci; the hyperbolic reflector being positioned and oriented with the convex reflector surface thereof intercepting the path of energy reflected from the second parabolic reflector and with the first focus thereof coinciding with the focus of the second parabolic reflector, for reflecting energy from the second parabolic reflector and concentrating said reflected energy at the second focus of the hyperbolic reflector.

10. A reflector system for concentrating energy at a point, comprising:
    a circular source generating energy radiated divergent from the source;
    a first elongated annular parabolic reflector having a reflector surface which is of concave parabolic profile in transverse cross-section and forms a circular focus, the first parabolic reflector being positioned and oriented with the circular focus thereof coincident with the circular source for intercepting energy from the source and reflecting the intercepted energy as a paraxial annular beam;
    a second elongated annular parabolic reflector having a reflector surface which is of concave parabolic profile in transverse cross-section and forms a focal point, the concave surface of the second parabolic reflector being positioned and oriented facing the first parabolic reflector for intercepting the path of the paraxial beam and reflecting and focusing the beam toward the focal point of the second parabolic reflector; and the second parabolic reflector having an aperture proximate the center thereof; and
    a circular hyperbolic reflector having a reflector surface which is of convex hyperbolic profile in transverse cross-section and having first and second foci; the hyperbolic reflector being positioned and oriented with the convex reflector surface thereof inside the first annular parabolic reflector and intercepting the path of energy reflected from the second parabolic reflector and with the first focal point thereof coinciding with the focal point of the second parabolic reflector, for reflecting energy from the second parabolic reflector through said aperture and concentrating said reflected energy at the second focal point of the hyperbolic reflector.

11. A reflector system for concentrating energy along a linear focus, comprising:
    a linear source generating energy radiated divergent from the source;
    a first elongated parabolic reflector having a reflector surface which is of concave parabolic profile in transverse cross-section and forms a linear focus, the first parabolic reflector being positioned and oriented with the linear focus thereof coincident with the linear source for intercepting energy from the source and reflecting the intercepted energy as a paraxial beam;
    a second elongated parabolic reflector having a reflector surface which is of concave parabolic profile in transverse cross-section and forms a linear focus, the concave surface of the second parabolic reflector being positioned and oriented facing the first parabolic reflector for intercepting the path of the paraxial beam and reflecting and focusing the beam toward the linear focus of the second parabolic reflector; and
    an elongated hyperbolic reflector having a reflector surface which is of convex hyperbolic profile in transverse cross-section and having first and second linear foci; the hyperbolic reflector being positioned and oriented with the convex reflector surface thereof intercepting the path of energy reflected from the second parabolic reflector and with the first linear focus thereof coinciding with the linear focus of the second parabolic reflector, for reflecting energy from the second parabolic reflector and concentrating said reflected energy along the second linear focus of the hyperbolic reflector.

12. A toroidal reflector system for concentrating energy at a point focus within the reflector, comprising:

an arcuate source forming at least a section of a circle in a plane orthogonal to the xy plane and parallel to the y axis and perpendicular to the x axis;

a cross-section of a reflector being defined in an xy plane and having a point focus located at the intersection of the x and y axes defining the xy plane, the reflector being described by rotation of said cross-section through a selected arc about said point focus and the x axis;

the reflector cross section comprising in the xy plane:

a primary parabolic reflector of concave parabolic profile forming a focal point, the source and the primary parabolic reflector being positioned and oriented such that the source intersects the xy axis at the point focus of the primary parabolic reflector as the reflector cross section is rotated about the x-axis, the primary parabolic reflector thereby intercepting energy from the source and reflecting the intercepted energy as a paraxial beam;

a secondary parabolic reflector of concave parabolic profile forming a point focus in the xy plane, said spr point focus forming an elongated arcuate focus as the reflector cross section is rotated about the x-axis, the concave surface of the secondary parabolic reflector thereby being positioned and oriented facing the first parabolic reflector for intercepting the path of the paraxial beam and reflecting and focusing the beam toward the focus of the secondary parabolic reflector; and a hyperbolic reflector adjacent the primary parabolic reflector, the hyperbolic reflector being of convex hyperbolic profile and having first and second point foci; the hyperbolic reflector being positioned and oriented with the convex reflector surface thereof intercepting the path of energy reflected from the secondary parabolic reflector and with the first focus thereof coinciding with the focus of the secondary parabolic reflector as the reflector cross section is rotated about the x-axis and thereby describing an arc; and the second focus thereof coinciding with the intersection of the x and y axes and said point focus, the hyperbolic reflector thereby reflecting energy from the secondary parabolic reflector and concentrating said reflected energy at said point focus.

13. A method for reflectively concentrating energy from a source to a point focus a distance removed from the source, comprising:

divergently radiating energy from an elongated source;

intercepting energy from the source with a first parabolic reflector and reflectively forming the energy into a paraxial beam;

intercepting the paraxial beam with a second parabolic reflector and reflectively focusing the energy comprising the paraxial beam toward a first focal point of a hyperbolic reflector having first and second focal points; and intercepting the energy directed toward the first focal point of the hyperbolic reflector with the hyperbolic reflector and reflectively focusing the energy to the second focal point of the hyperbolic reflector.

* * * * *